United States Patent
Von Berg et al.

(10) Patent No.: US 12,217,419 B2
(45) Date of Patent: Feb. 4, 2025

(54) INHALATION METRIC FOR CHEST X-RAY IMAGES

(71) Applicant: KONINKLIJKE PHILIPS N.V., Eindhoven (NL)

(72) Inventors: Jens Von Berg, Hamburg (DE); Daniel Bystrov, Hamburg (DE); Sven Kroenke, Hamburg (DE); Stewart Young, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/641,122

(22) PCT Filed: Sep. 1, 2020

(86) PCT No.: PCT/EP2020/074262
§ 371 (c)(1),
(2) Date: Mar. 8, 2022

(87) PCT Pub. No.: WO2021/047941
PCT Pub. Date: Mar. 18, 2021

(65) Prior Publication Data
US 2024/0046452 A1 Feb. 8, 2024

(30) Foreign Application Priority Data
Sep. 9, 2019 (EP) .................................. 19196143

(51) Int. Cl.
*G06K 9/00* (2022.01)
*A61B 6/00* (2006.01)
*A61B 6/50* (2024.01)
*G06T 7/00* (2017.01)

(52) U.S. Cl.
CPC .............. *G06T 7/0012* (2013.01); *A61B 6/50* (2013.01); *A61B 6/5217* (2013.01);
(Continued)

(58) Field of Classification Search
CPC ......... G06T 7/0012; G06T 2207/10116; G06T 2207/20081; G06T 2207/30008; G06T 2207/30168; A61B 6/50; A61B 6/5217
See application file for complete search history.

(56) References Cited

U.S. PATENT DOCUMENTS

| | | | |
|---|---|---|---|
| 8,953,856 B2 | 2/2015 | Ostrovsky-Berman | |
| 2004/0234133 A1* | 11/2004 | Bohm | G06T 7/194 382/199 |
| 2006/0285751 A1* | 12/2006 | Wu | G06V 10/26 382/199 |
| 2009/0087072 A1* | 4/2009 | Hong | G06T 7/12 382/132 |

(Continued)

FOREIGN PATENT DOCUMENTS

WO   WO-2017080868 A1 *   5/2017   ............... A61B 6/50

OTHER PUBLICATIONS

Fast and robust diaphragm detection and tracking in cardiac x-ray projection images, Alexandru Condurache et al., SPIE, 2005, pp. 1766-1775 (Year: 2005).*

(Continued)

*Primary Examiner* — Jayesh A Patel
(74) *Attorney, Agent, or Firm* — Larry Liberchuk (57) ABSTRACT

In order to enhance enhanced X-ray image inhalation quality monitoring, a metric is proposed hat reproducibly provides an index of ribs visible to be used in the assessment of the inhalation state. In an example, a detected diaphragm in a chest X-ray image may be projected into an atlas that contains labels for all intercostal spaces, namely spaces between rib centerlines. A spatial representation of both the clavicle and the ribs is provided in the atlas, a cumulative histogram is built for all points, i.e. pixels, of the diaphragm, for every point a rib label counter of the rib in the rib label map at that point is incremented as well as all ribs above it, the rib label counter is normalized by a division by the number of points, the median (or a different quantile) may (Continued)

be taken of this distribution serving as an inhalation index. An objective metric of inhalation state is thus achieved.

13 Claims, 4 Drawing Sheets

(52) U.S. Cl.
CPC ............... *G06T 2207/10116* (2013.01); *G06T 2207/20081* (2013.01); *G06T 2207/30008* (2013.01); *G06T 2207/30168* (2013.01)

(56) References Cited

U.S. PATENT DOCUMENTS

2013/0156267 A1* 6/2013 Muraoka .............. A61B 6/5217 382/103
2018/0325481 A1* 11/2018 Young .................. A61B 6/5217

OTHER PUBLICATIONS

Diaphragm border detection in coronary X-ray angiographies New method and applications, Simeon Petkov et al., ELSEVIER, 2014, pp. 296-305 (Year: 2014).*

Atlas-based rib-bone detection in chest X-rays, Sema Candemir et al., ELSEVIER, 2016, pp. 32-39 (Year: 2016).*

Automatic Delineation of the Diaphragm in Computed Tomographic Images, Rangaraj M. Rangayyan et al., JODI, 2008, pp. S134-S147 (Year: 2008).*

Robust and Accurate Diaphragm Border Detection in Cardiac X-Ray Angiographies, Simeon Petkov et al., Springer, 2013, pp. 225-234 (Year: 2013).*

PCT International Search Report, International application No. PCT/EP2020/074262, Nov. 17, 2020.

Park M. et al., "Detection and Labeling Ribs on Expiration Chest Radiographs", Proceedings of SPIE/ IS & T, vol. 5030, Jan. 1, 2003 (Jan. 1, 2003), pp. 1021-1031, XP009107629.

Carmichael J H E et al., "European Guidelines on Quality Criteria for Diagnostic Radiographic Images", Office for Official Publications of the European Communities, (EuropGuideline), 1996.

Candemir S. et al., "Atlas-Based Rib-Bone Detection in Chest X-Rays", Computerized Medical Imaging and Graphics, vol. 51, pp. 32-39, 2016.

Mader A.O. et al., "Localization and Labeling of Posterior Ribs in Chest Radiographs Using a CRF-Regularized FCN with Local ", Medical Image Computing and Computer Assisted Intervention— MICCAI, pp. 562-570, 2018.

* cited by examiner

Fig. 5

INHALATION METRIC FOR CHEST X-RAY IMAGES

FIELD OF THE INVENTION

The present invention relates to X-ray image inhalation quality monitoring, and in particular to a method for X-ray image inhalation quality monitoring, an apparatus for X-ray image inhalation quality monitoring, an X-ray imaging system, a computer program element, and a computer readable medium.

BACKGROUND OF THE INVENTION

Chest X-ray examination is an important procedure for detecting and monitoring of lung abnormalities and diseases at an early stage in the lungs of patients. Medical personnel, such as doctors or radiologists, detect abnormalities directly from X-ray images. Assessing the image quality directly after acquisition is the task of a medical imaging professional. The image is checked as being of sufficient quality before the patient leaves the examination room. If the chest X-ray image is not of sufficient quality, a new image should be taken before the patient leaves the examination room. Image quality is dependent upon the skill of the system operator. US 2018/0325481 A1 discusses the assessment of the quality of an image according to a rib intersection rule. However, several posterior ribs may intersect with the diaphragm, thereby making this task inherently ambiguous.

US 2013/156267 A1 discloses a diagnosis assistance system.

SUMMARY OF THE INVENTION

There may be a need to provide a technique for enhanced X-ray image inhalation quality monitoring.

The object of the present invention is solved by the subject matter of the independent claims, wherein further embodiments are incorporated in the dependent claims. It should be noted that the following described aspects of the invention apply also for the method, the apparatus, the X-ray imaging system, the computer program element, and the computer readable medium.

A first aspect of the present invention provides a computer implemented method for X-ray image inhalation quality monitoring. The method comprises the following steps:
a) receiving a chest X-ray image of a patient;
b) detecting rib bones in the chest X-ray image;
c) identifying a plurality of intercostal spaces each representing a space between adjacent detected rib bones;
d) detecting the diaphragm in the chest X-ray image and generating a diaphragm line comprising a plurality of points representing a path of a diaphragm in the chest X-ray image; and
e) applying a score assigning rule to assign a point score to each point of the diaphragm line based on a respective intercostal space where the point is located in the image, wherein the score assigning rule defines a correspondence between point scores to be assigned depending on the intercostal spaces where the point is located; and
f) determining an inhalation index based on the point scores of the points of the diaphragm line.

In other words, a chest X-ray image is assessed to determine the locations of the points of the diaphragm with respect to the intercostal spaces. Each point of the diaphragm is associated with a respective point score in accordance to the intercostal space where the point is located. For example, each intercostal space may be labelled, e.g., denoted "1" to "10". The point score of a point may be associated with the label of a respective intercostal space where the point is located. For example, if the point is located in an intercostal space with the label "10", then a point score of "10" is assigned to this point. Thus, if there is an intersection of a rib bone with the diaphragm, the diaphragm may have points with different point scores. As higher quality images and lower quality images have different intersection conditions, the diaphragm in the good quality images has a different point score distribution along the diaphragm line compared to that in the bad quality images. Thus, the inhalation index may be determined based on the point score distribution along the diaphragm. In some examples, this may be reduced to come with a simple overall value, such as an average value, or a median, of the point scores of all points of the diaphragm. In this way, a unique metric is provided that give an index of ribs visible above the diaphragm. Finally, the image quality may be assessed according to the computed inhalation index. In an example, an operator may use the inhalation index to gauge the quality of the image themselves. In another example, the inhalation index may be further categorised into three groups of "bad, medium, good" according to a pre-determined X-ray image inhalation quality monitoring rule as described below.

Thus, the proposed method may achieve a more reliable and easier assessable determination of the image quality of a chest X-ray image. The computation of the inhalation index for each chest X-ray image may be carried out without human supervision or interference, thereby avoiding the dependency upon variations or biases in the skill level of different system operators. The automated quantification of the inspiration status of the patient may also be integrated into an automated radiological interpretation and reporting process. Thus, the success rate of medical imaging may be improved, and the assessment process may be simplified.

As used herein, the term "rib bones", or "ribs", may refer to an X-ray projection of a rib onto an X-ray detector, thus forming an X-ray image of the rib. Thus, the term "rib centerlines" defines lines of the X-ray image, which correspond to the shape of a rib bone in a patient. Dependent on the imaging angle, and the image type, and the extent of patient inspiration or expiration, the rib centerlines may be more or less curved, and may intersect with the diaphragm, or other rib centerlines.

As used herein, the term "intercostal space" may refer to a space between adjacent rib centerlines.

As used herein, the term "diaphragm" may refer to an X-ray projection of a diaphragm onto an X-ray detector, hence forming an X-ray image of the diaphragm, for example from the posterior or anterior body direction. Thus, the term "diaphragm line" defines a path in the X-ray image which tracks the shape of the trace of a diaphragm in the X-ray image. The diaphragm typically appears as a cup-shaped boundary at the bottom of the lung lobes, although the boundary may move, dependent upon the extent to which the chest cavity is enlarged.

As used herein, the term "score assigning rule" defines a correspondence between point scores and intercostal spaces. For example, a lookup table may be used to define an association between point scores and the intercostal spaces. Once it is determined in which intercostal space the point is located, each intercostal space may be checked for equality in turn and the associated point score, if any, will be used as a result of the search, i.e., a point score assigned to this point. In another example, each intercostal space may be labelled, e.g., denoted "1" to "10". The point score of a point may be associated with the label of a respective intercostal space where the point is located. For example, if one point is located in an intercostal space with the label "10", then a point score of "10" is assigned to this point.

According to an embodiment of the present invention, the method further comprises comparing the determined inhalation index with a pre-determined X-ray image inhalation quality monitoring rule specifying an image inhalation state in terms of the inhalation index, to yield an X-ray image inhalation quality measure.

The pre-determined X-ray image inhalation quality monitoring rule may enable the determination of whether or not a good, or a bad, image is present. The pre-determined X-ray image inhalation quality monitoring rule may divide the values of the inhalation index into two or more categories. Each category corresponds to a particular value range of the inhalation index, e.g., selected from the group of "bad, medium, good". For example, the category "good" corresponds to the inhalation index ranging from 9 to 10, the category "medium" corresponds to the inhalation index ranging from 8 to 9, and the category "bad" corresponding to the remaining inhalation index. The X-ray image inhalation quality measure may be output on a display, such as a computer display screen, or a display of a mobile device. In another example, the X-ray image inhalation quality measure may be output as an illuminated warning light, or a warning sound. In a further example, the X-ray image inhalation quality measure may be output as a bitmap "watermark" inserted in a portion of an X-ray image provided by an X-ray apparatus or just stored in the meta data (DICOM tags) of the image.

This may facilitate a system operator to determine the image quality compared to the continuous value of the inhalation index.

According to an embodiment of the present invention, step b) further comprises:
  b1) building a statistical atlas by co-registration of training images that comprise a plurality of chest X-ray images of one or more patients; and
  b2) registering the statistical atlas with the chest X-ray image of the patient to build a patient specific rib-bone model of the patient.

In other words, one or more rib-bone atlases may be used for automatic detection of rib-bones in the chest X-ray image. The aim of the statistical atlas is to build a rib-bone model for the patient X-ray using other patient X-rays with their corresponding rib-bone models. The use of a patient specific atlas of the ribs or equivalently the intercostal spaces may robustly account for an inherent ambiguity resulting from the situation where several posterior ribs intersect with the diaphragm.

A statistical atlas may be built by co-registration of training images. In this atlas, a rib index is assigned for each position by construction. Then, this atlas is registered with the chest X-ray image and thus a rib index for each pixel in the chest X-ray image is created. In other words, an algorithm may compute the corresponding pixels between the statistical atlas and the chest X-ray images. Then, the rib model in the statistical atlas is aligned to the chest X-ray image by applying a transformation mapping.

According to an embodiment of the present invention, in step c) the plurality of intercostal spaces is identified in the patient specific rib-bone model.

In other words, the intercostal space may be identified in the atlas space.

According to an embodiment of the present invention, step d) further comprises:
  d1) mapping the detected diaphragm into the patient specific rib-bone model to generate the diaphragm line based on the registration.

For example, the diaphragm may be detected by gradient detection, texture detection of regions inside the thorax, a water-filling algorithm, or by deploying knowledge learned from training images concerning the expected shapes to be found in the chest X-ray image, e.g. by convolutional neural networks.

In step d1) the detected diaphragm may be mapped into the patient specific rib-bone model using the mapping parameters of the above-mentioned transformation mapping.

According to an embodiment of the present invention, in step f) the inhalation index is determined based on the point scores of the points of a right lung diaphragm line representing a path of the diaphragm in a right lung field portion and/or a left lung diaphragm line representing a path of the diaphragm in a left lung field portion.

In other words, the inhalation index may be gather for a right or a left lung in isolation.

According to an embodiment of the present invention, the method further comprises:
  labelling the plurality of intercostal spaces with intercostal labels; and/or
  labelling the detected rib bones with rib labels;
  wherein the score assigning rule defines:
  (i) a correspondence between point scores and intercostal labels; and/or
  (ii) a correspondence between point scores and rib labels.

For example, if a point falls inside the tenth intercostal space, a point score of "10" may be assigned to this point. For example, if a point falls inside an intercostal space between the ninth and tenth ribs, a point score of "9.5", i.e., an average of the labels of the ninth and tenth ribs, may be assigned to this point.

According to an embodiment of the present invention, the score assigning rule further defines a correspondence between point scores and a spatial relation of a point in an intercostal space with respect to two detected rib bones that define the intercostal space. Alternatively, the score assigning rule provides interpolated rib labels and/or interpolated intercostal labels at each position in the statistical atlas such that a point score can be obtained for a given image pixel of the chest X-ray image by registering the statistical atlas with the chest X-ray image.

In other words, the point score of a point may be spatially interpolated on its relative position inside the intercostal space. For example, if the point is in the middle of the ninth intercostal space, its point score may be "9". If the point is located at the upper rib bone of the ninth intercostal space, its point score may be "8.5". If the point is located at the lower rib bone of the ninth intercostal space, its point score may be "9.5". This may further improve the accuracy of estimating the position of each point of the diaphragm with respect to the respective intercostal space. Alternatively, the statistical atlas may provide interpolated rib labels and/or interpolated intercostal labels at each position in the atlas space. The interpolated rib labels and/or interpolated intercostal labels in the atlas space may be then mapped to respective image pixels in the chest X-ray image by applying a transformation mapping, i.e. using the registration. In this way, a point score can be directly read out for a given image pixel in the chest X-ray image using the transformation.

According to an embodiment of the present invention, the inhalation index comprises at least one of measures of central tendency of the point scores of the diaphragm line.

Examples of measures of central tendencies may include the mean, median, and mode. Thus, the complexity of monitoring the point score distribution along the diaphragm line may be reduced to come with a simple overall value.

A second aspect of the present invention provides an apparatus for X-ray image inhalation quality monitoring. The apparatus comprises:
- an input unit; and
- a processing unit;
- wherein the input unit is configured to receive a chest X-ray image of a patient;
- wherein the processing unit is configured for:
- detecting rib bones in the chest X-ray image;
- identifying a plurality of intercostal spaces each representing a space between adjacent detected rib bones;
- detecting the diaphragm in the chest X-ray image and generating a diaphragm line comprising a plurality of points representing a path of a diaphragm in the chest X-ray image; and
- applying a score assigning rule to assign a point score to each point of the diaphragm line based on a respective intercostal space where the point is located in the image, wherein the score assigning rule defines a correspondence between point scores to be assigned depending on the intercostal spaces where the point is located; and
- determining an inhalation index based on the point scores of the points of the diaphragm line.

Therefore, an apparatus is provided having advantages similar to the first aspect discussed above.

According to an embodiment of the present invention, the processing unit is further configured to compare the determined inhalation index with a pre-determined X-ray image inhalation quality monitoring rule specifying an image inhalation state in terms of the inhalation index, to yield an X-ray image inhalation quality measure.

This may facilitate a system operator to determine the image quality.

According to an embodiment of the present invention, an output unit configured to output at least one of the determined inhalation index and the X-ray image inhalation quality measure.

In an example, the output unit may be configured to output at least one of the determined inhalation index and the X-ray image inhalation quality measure on a display. Therefore, the inhalation index and/or the X-ray image inhalation quality measure may be displayed to a medical professional. In another example, the determined inhalation index and/or the X-ray image inhalation quality measure may be output as an illuminated warning light, or a warning sound. In a further example, the determined inhalation index and/or the X-ray image inhalation quality measure may be output as a bitmap "watermark" inserted in a portion of an X-ray image provided by an X-ray apparatus or just stored in the meta data (DICOM tags) of the image.

A third aspect of the present invention provides an X-ray imaging system. The X-ray imaging system comprises:
- an X-ray image acquisition device with an X-ray source and an X-ray detector; and
- an apparatus as above and below described;
- wherein the X-ray image acquisition device is configured to acquire chest X-ray image data of the patient, and to provide the X-ray imaging data to the apparatus for X-ray image inhalation quality monitoring.

Therefore, an X-ray imaging system having the ability to provide a lung image quality assessment to a user is provided.

According to a fourth aspect of the invention, there is provided a computer program element for controlling an apparatus as above and below described. When being executed by the processing unit, the computer program element is adapted to perform the method steps as described above and below.

According to a fifth aspect of the present invention, there is provided a computer-readable medium having stored the computer program element as described above and below.

These and other aspects of the present invention will become apparent from and be elucidated with reference to the embodiments described hereinafter.

Definitions

"user" as used herein is medical personnel at least partly involved in an administrative or organizational manner in the imaging procedure.

"patient" is a person, or in veterinary settings, an animal (in particular a mammal), who is imaged.

BRIEF DESCRIPTION OF THE DRAWINGS

These and other aspects of the invention will be apparent from and elucidated further with reference to the embodiments described by way of examples in the following description and with reference to the accompanying drawings, in which.

It should be noted that the figures are purely diagrammatic and not drawn to scale. In the figures, elements, which correspond to elements already described, may have the same reference numerals. Examples, embodiments or optional features, whether indicated as non-limiting or not, are not to be understood as limiting the invention as claimed.

DETAILED DESCRIPTION OF EMBODIMENTS

A chest X-ray acquisition is typically performed with a patient having inhaled completely and holding breath. In images not compliant to this rule, the lung parenchyma may look different, tissue may cluster to form opacities that can easily be taken as sign of an abnormality. The European guideline on X-ray acquisition states that a posterior-anterior (PA) chest should be "performed at full inspiration (as assessed by the position of the ribs above the diaphragm—either 6 anteriorly or 10 posteriorly) and with suspended respiration".

When assessing image quality with respect to the patient inhalation state, a radiologist often decides intuitively and only counts in cases of doubt. In order to automate this task, algorithms can be used to do the assessment of image quality criteria like the inhalation state. An automatic quality check may be more reproducible, more robust, and more accurate. When implementing the guideline in an algorithm it turns out that counting ribs above the diaphragm is not easily possible. Typically, the ribs close to the diaphragm intersect with it instead of being located either clearly above or below it.

Figure 1A:
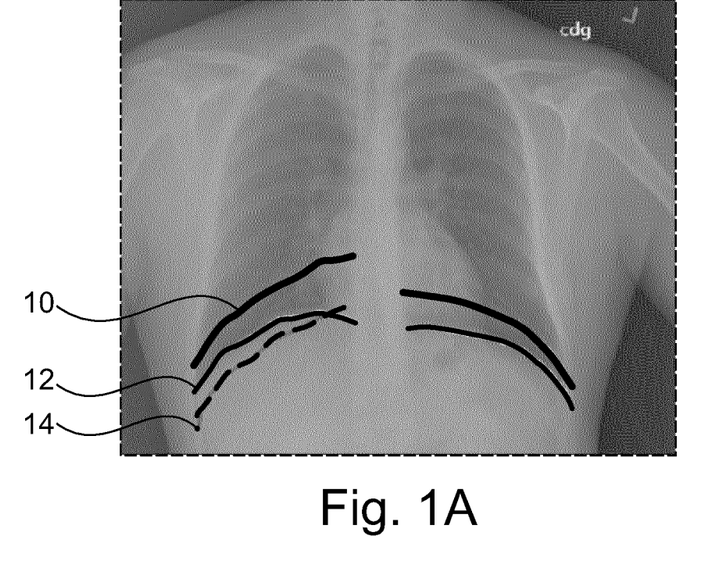
FIG. 1A shows an example of a chest X-ray image.
Figure 1B:
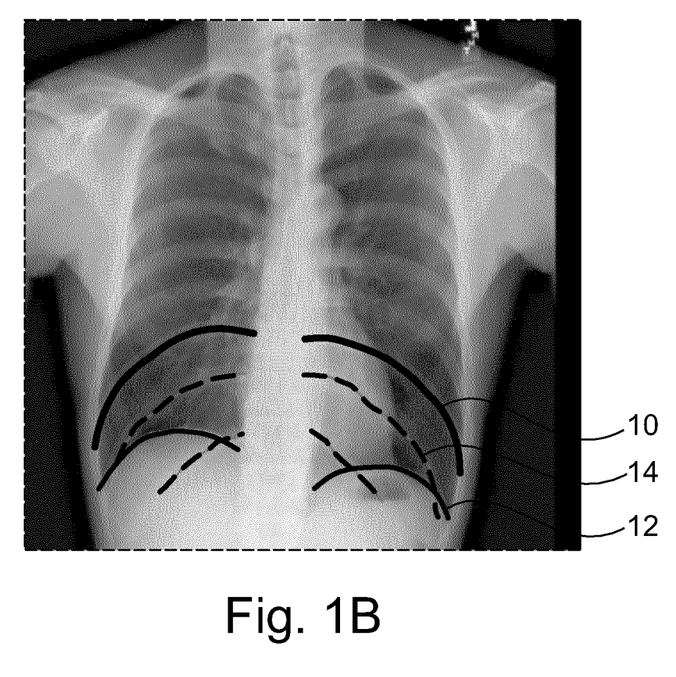
FIG. 1B shows another example of a chest X-ray image.

For example, FIGS. 1A and 1B shows two examples of chest X-ray images. In particular, FIG. 1A shows a case where the decision is still quite easy. In this case the rib centerlines 10 do not intersect with the diaphragm 12. Only rib centerlines 14 might be considered intersecting. FIG. 2B shows a case where depending on the criterion when to consider a rib above the diaphragm may results in a difference of two rib counts on both sides. In this case two rib centerlines 14 on both sides intersect with the diaphragm 12 and the only ones fully above the diaphragm are the rib centerlines 10.

Figure 2:
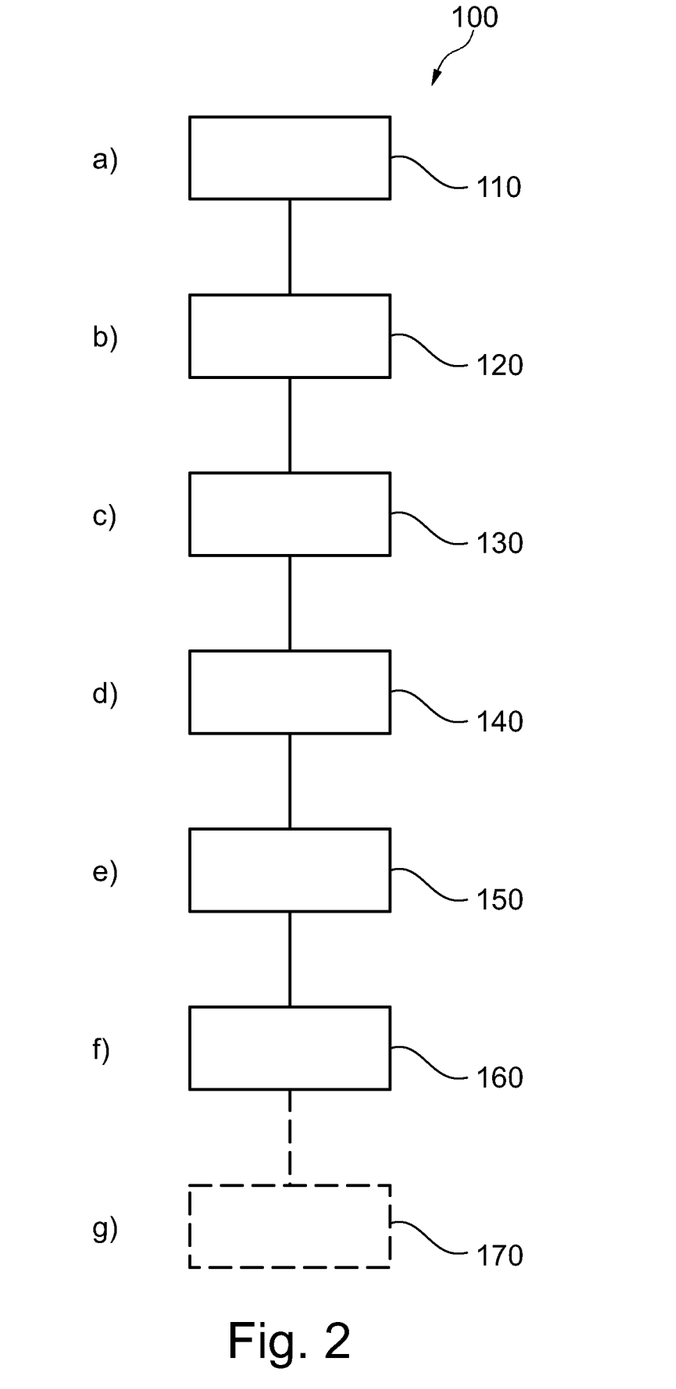
FIG. 2 shows a flowchart representative of a method of X-ray image inhalation quality monitoring according to some embodiments of the present disclosure.

FIG. 2 shows a flowchart representative of a method 100 for enhanced X-ray image inhalation quality monitoring according to some embodiments of the present disclosure.

In step 110, i.e. step a), a chest X-ray image of a patient is received. In an example, the chest X-ray image may be received from a digital recording plate, namely a digital flat-panel X-ray detector. In another example, the X-ray image may be received from a digital scanning apparatus for scanning a film-exposure of the region of interest.

In step 120, i.e. step b), rib bones are detected in the chest X-ray image. There is a number of methods to segment ribs in chest radiographs. In an example, an edge-based method may be used to detect rib bones. This method first extracts the rib pixels using an edge detection algorithm, and then groups the candidate pixels/lines into a complete rib boundary by applying e.g., a curve fitting technique or a geometric model such as parabolas. In another example, a classification scheme is used to classify rib/non-rib pixels. For example, the posterior ribs in chest radiographs may be segmented using iterated contextual pixel classification. Starting from an initial rib segmentation obtained from pixel classification, this method updates it by reclassifying every pixel, based on the original features and, additionally, class label information of pixels in the neighborhood of the pixel to be re-classified. In a further example, a prior-information based segmentation method may be used to detect rib bones. One way to incorporate prior knowledge is to use a prototype atlas, which comprises a set of model chest X-ray images and their corresponding rib-bone boundaries.

Figure 3A:
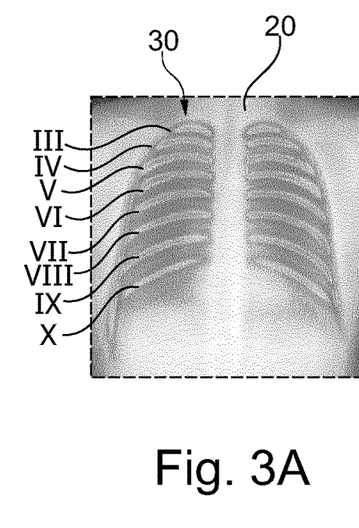
FIG. 3A shows an example of a patient specific rib-bone model.

An exemplary implementation of the atlas is described in conjunction with FIG. 3A, which illustrates a patient specific rib-bone model 20 of the patient. To build the patient-specific rib-bone model, a statistical atlas is built by co-registration of training images that comprise a plurality of chest X-ray images of one or more patients. The training images may have manually delineated rib-bone boundaries. Each pixel in the statistical atlas may be assigned with a rib index by construction. Then, the statistical atlas is registered with the chest X-ray image of the patient to build a patient specific rib-bone model of the patient. In other words, the statistical atlas is registered to the chest X-ray image of the patient, yielding a transformation for each pixel, which allows the corresponding atlas rib mask to be transformed and treated as segmentation for the rib-bone of the patient. In this way, a rib index for each pixel is transformed from the statistical atlas to the chest X-ray image, thus forming a patient-specific rib-bone model in form of a density of rib centerlines 30 in the atlas space.

Optionally, as illustrated in FIG. 3A, the rib bones may be numbered using a rib-labelling algorithm. For example, the rib centerlines 30 may be labelled according to their rib position. Conventionally, the rib nearest a patient head is denoted "1". The "true ribs" depend downwards as ribs 1 to 7. The "false ribs" 8 to 12 depend onwards. Ribs 11 and 12 are sometimes known as "floating ribs".

In step 130, i.e. step c), a plurality of intercostal spaces is identified. Each intercostal space represents a space between adjacent detected rib bones.

In an example, if an edge-based method or a classification scheme is used for rib-bone detection in step b), the intercostal space may be identified in the chest X-ray image.

In another example, if an atlas is used for rib-bone detection, the intercostal space may be identified in the patient specific rib-bone model of the patient.

Figure 3B:
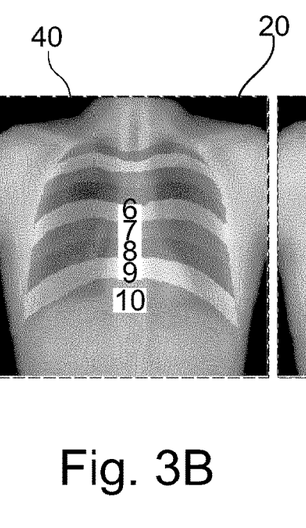
FIG. 3B shows an example of a patient specific rib-bone model with identified intercostal spaces.

An exemplary implementation of the atlas for identifying intercostal spaces is described in conjunction with FIG. 3B. In this example, the plurality of intercostal spaces 40 is identified in the patient specific rib-bone model 20 in FIG. 3A. Each intercostal space 40 corresponds to a respective space between adjacent rib centerlines 30.

Optionally, as illustrated in FIG. 3B, the intercostal spaces may be numbered using an intercostal-space-labelling algorithm. For example, the intercostal space below the rib centerline X is denoted "10". The intercostal space between the rib centerline IX and X is denoted "9".

In step 140, i.e. step d), a diaphragm line representing a path of a diaphragm in the chest X-ray image is generated. Typically, in the chest X-ray image, the region of interest is a human thorax. The diaphragm follows a curved path through the bottom of the thorax area. The diaphragm divides different textures of tissue, and has a distinct shape, having a right-hand-side "dome" which is slightly higher than a dome of the left side of the diaphragm. Therefore, a line following the path of the diaphragm in the chest X-ray image is amenable to detection by image processing techniques. Although a human diaphragm is a single, connected boundary, it is possible to detect distinct sessions of the diaphragm, such as a left section and a right section.

The diaphragm may be detected by gradient detection, texture detection of regions inside the thorax, a water-filling algorithm, or by deploying knowledge learned from training images concerning the expected shapes to be found in the image. The shape of the diaphragm follows a curved line, and is thus amenable to modelling using a spline approach.

Figure 3C:
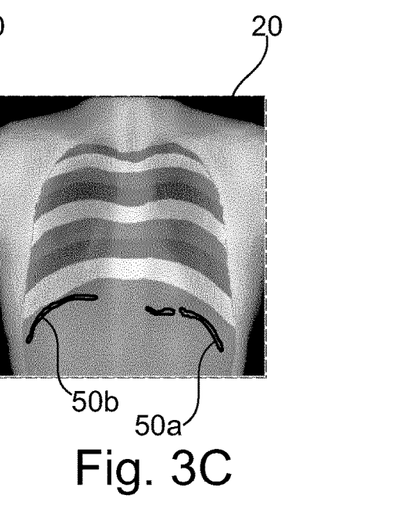
FIG. 3C shows an example of a patient specific rib-bone model with an identified diaphragm.
Figure 3D:
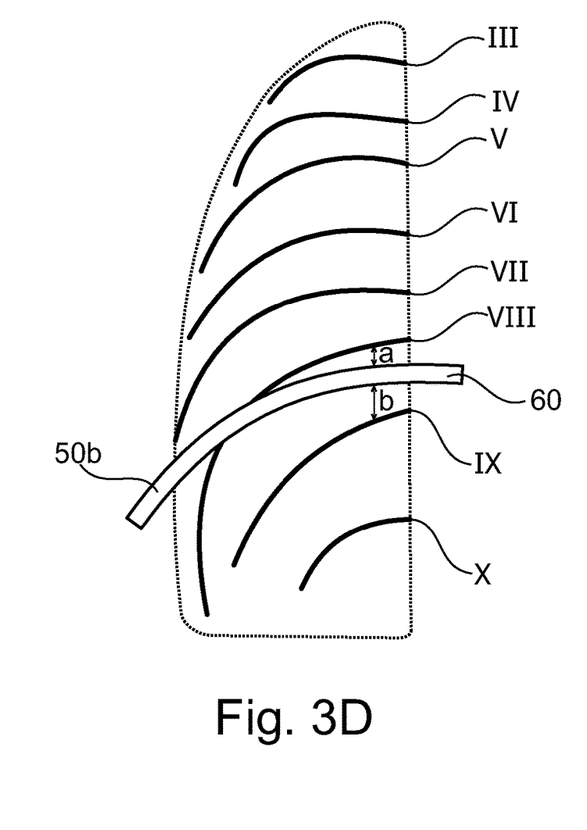
FIG. 3D shows an exemplary implementation of the correspondence between the point scores and the position within the respective intercostal space.

An exemplary example of a diaphragm is described in conjunction with FIG. 3C. Similar to FIGS. 3A and 3B, the diaphragm 50 is provided in the atlas space. This may be done firstly by detecting the diaphragm in the chest x-ray image, e.g., by gradient detection, or a water-filling algorithm, and then by mapping the detected diaphragm into the atlas space with the same mapping based on the registration in FIG. 3A. In the illustrated example in FIG. 3C, both the left lung diaphragm line 50a and the right lung diaphragm line 50b are located in the tenth intercostal space. In some examples, such as a thoracic X-ray showing bad-quality inspiration as illustrated in FIG. 3D, the left lung diaphragm line 50a may be located in two or more intercostal spaces.

In step 150, i.e., step e), a score-assigning rule is applied to assign a point score to each point of the diaphragm line based on a respective intercostal space where the point is located. The score-assigning rule defines a correspondence between point scores and intercostal spaces.

For example, the score-assigning rule may define a correspondence between point scores and intercostal labels. In an example, the point score of one point of the diaphragm line is equal to the label of the intercostal space where that point is located. For example, if one point of the diaphragm line is located with the tenth intercostal space, a point score of "10" is then assigned to this point. In the exemplary example of FIG. 3C, as the left lung diaphragm line 50*a* is located in the tenth intercostal space, the points of the left lung diaphragm line 50*a* will be assigned with a point score of "10". This also applies to the right lung diaphragm line 50*b*. In another example, the score-assigning rule may define that a correspondence between point scores and rib labels, e.g., that the point score of one point of the diaphragm line is equal to an average of the rib labels of the adjacent ribs that defines the intercostal space where the point is located.

Optionally, the score-assigning rule may further define a correspondence between point scores and a spatial relation of a point in an intercostal space with respect to two detected rib bones that define the intercostal space. In other words, the point score of a point may be further adjusted based on its relative position in the intercostal space. An exemplary implementation of the correspondence between the point scores and the position within the respective intercostal space is illustrated in FIG. 3D, which illustrates a simple version of a right half of a thorax cavity with a level of inspiration which would result in a poor quality image. A point 60 of the diaphragm line 50*b* is located between the eighth rib centerline and the ninth rib centerline. The point 60 has a distance "a" from the eighth rib centerline and a distance "b" from the ninth rib centerline. In an example, the point score of this point 60 may be calculated using the following formula:

$$\text{point score} = x + \frac{a-b}{a+b} \cdot 0.5$$

where x is the intercostal label of the intercostal space where the point is located.

Alternatively, the score assigning rule provides interpolated rib labels and/or interpolated intercostal labels at each position in the statistical atlas such that a point score can be obtained for a given image pixel of the chest X-ray image by registering the statistical atlas with the chest X-ray image. For example, the atlas provides interpolated rib indices at each position that may be directly read out for a given image pixel using the transformation.

In step 160, i.e., step f), an inhalation index is determined based on the point scores of the points of the diaphragm line. Optionally, the inhalation index may be determined based on the point scores of the points of a right lung diaphragm line 50*b* representing a path of the diaphragm in a right lung field portion and/or a left lung diaphragm line 50*a* representing a path of the diaphragm in a left lung field portion.

Examples of the inhalation index may include, but not limited to, the mean, median, and mode of the point scores, i.e., the pixels, of the diaphragm line. In an example, a cumulative histogram may be built for all points of the left and/or right diaphragm lines. For every point the rib label counter of the rib in the rib label map at that point is incremented as well as all ribs above it. Having all points processed, all rib label counters may be normalized by a division by the number of the points, thereby having a value ranging between 0 and 1. Finally, the median (or mode) may be taken of this distribution serving as the inhalation index.

Optionally, the inhalation index may be output. In an example, the inhalation index may be output on a display, such as a computer display screen. This may allow an operator to gauge the quality of the image themselves. In another example, the inhalation index may be output for further analysis, e.g., for yielding an X-ray image inhalation quality measure as explained below.

Optionally, step 170, i.e. step g) may be provided for comparing the determined inhalation index with a predetermined X-ray image inhalation quality monitoring rule specifying an image inhalation state in terms of the inhalation index, to yield an X-ray image inhalation quality measure.

The X-ray inhalation quality monitoring rule may be provided as data records linked to specific imaging standards, such as the "European Guidelines on Quality Criteria for Diagnostic Images", to enable regional or national imaging standards to be followed. Alternatively or additionally, the X-ray image inhalation quality monitoring rule may be pre-programmed by a medial imaging professional, either to a pre-defined standard, or to a specific protocol required by a healthcare facility.

The X-ray image inhalation quality measure may be a discretized category, for example selected from the group of "bad, medium, good". Each category of the X-ray image inhalation quality measure may correspond to a particular range of the inhalation index. For example, the category "good" corresponds to the inhalation index ranging from 9.2 and upper, the category "medium" corresponds to the inhalation index ranging from 8.1 to 9.2, and the category "bad" corresponding to the remaining inhalation index. The X-ray image inhalation quality measure may be a continuous value, for example a percentage. This may allow an experienced operator to gauge the quality of the image themselves.

Optionally, the X-ray image inhalation quality measure may be output. For example, the X-ray image inhalation quality measure may be output on a display, such as a computer display screen, or a display of a mobile device. In another example, the X-ray image inhalation quality measure may be output as an illuminated warning light, or a warning sound. In a further example, the X-ray image inhalation quality measure may be output as a bitmap "watermark" inserted in a portion of an X-ray image provided by an X-ray apparatus.

Figure 4:
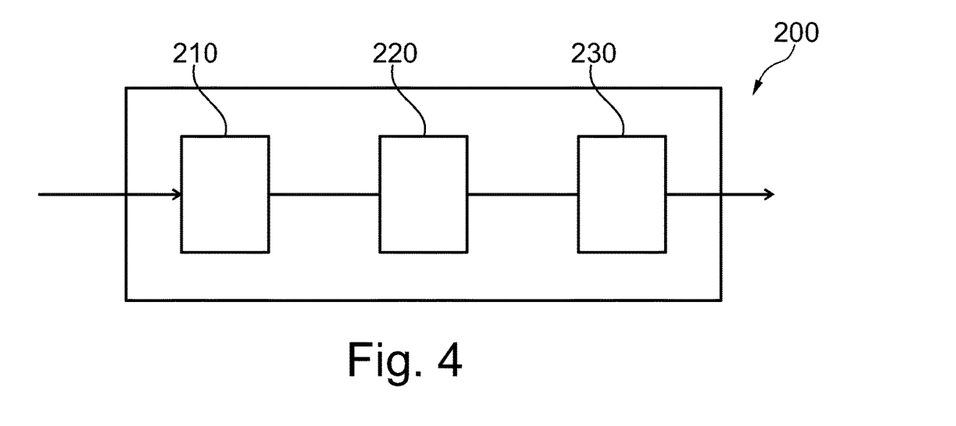
FIG. 4 shows a schematic block diagram of an exemplary implementation of an apparatus for X-ray image inhalation quality monitoring according to some embodiments of the present disclosure.

FIG. 4 shows a schematic block diagram of an exemplary implementation of an apparatus 200 for X-ray image inhalation quality monitoring according to some embodiments of the present disclosure.

The apparatus 200 comprises an input unit 210 and a processing unit 220. The apparatus 200 may be part of, or include an Application Specific Integrated Circuit (ASIC), an electronic circuit, a processor and/or memory that execute one or more software or firmware programs, a combinational logical circuit, and/or other suitable components that provide the described functionality.

The input unit 210 is configured to receive a chest X-ray image of a patient, e.g., from an analog or digital X-ray detector.

The processing unit 220 is configured for detecting rib bones in the chest X-ray image, e.g., using an edge detection algorithm, a classification scheme, or a prior-information based segmentation method, such as an atlas based segmentation method. For example, the processing unit 220 may be configured for building a statistical atlas by co-registration of training images that comprise a plurality of chest X-ray images of one or more patients, and registering the statistical atlas with the chest X-ray image of the patient to build a patient specific rib-bone model of the patient.

The processing unit 220 is further configured for identifying a plurality of intercostal spaces. Each intercostal space represents a space between adjacent detected rib bones. In an example, the processing unit 220 may be configured for identifying the plurality of intercostal spaces in the patient specific rib-bone model.

The processing unit 220 is further configured for generating a diaphragm line representing a path of a diaphragm in the chest X-ray image. The diaphragm may be detected by gradient detection, texture detection of regions inside the thorax, a water-filling algorithm, or by deploying knowledge learned from training images concerning the expected shapes to be found in the image. Optionally, the processing unit 220 may be configured for detecting the diaphragm in the chest X-ray image, e.g., using gradient detection, or a water-filling algorithm, and mapping the detected diaphragm into the patient specific rib-bone model to generate the diaphragm line based on the registration.

The processing unit 220 is further configured for applying a score assigning rule to assign a point score to each point of the diaphragm line based on a respective intercostal space where the point is located. The score assigning rule defines a correspondence between point scores and intercostal spaces. For example, the processing unit 220 may be configured for labelling the plurality of intercostal spaces with intercostal labels and/or labelling the detected rib bones with rib labels. The score assigning rule may define (i) a correspondence between point scores and intercostal labels and/or (ii) a correspondence between point scores and rib labels. Optionally, the score assigning rule may further define a correspondence between point scores and a spatial relation of a point in an intercostal space with respect to two detected rib bones that define the intercostal space.

The processing unit 220 is further configured for determining an inhalation index based on the point scores of the points of the diaphragm line. The inhalation index comprises at least one of measures of central tendency, such as the mode, median, or the mean, of the point scores of the diaphragm line.

Optionally, the processing unit 220 may be further configured to compare the determined inhalation index with a pre-determined X-ray image inhalation quality monitoring rule specifying an image inhalation state in terms of the inhalation index, to yield an X-ray image inhalation quality measure, which may be a discretized category, for example selected from the group of "bad, medium, good".

Optionally, the apparatus 200 may further comprise an output unit 220. The output unit 220 may be configured to output at least one of the determined inhalation index and the X-ray image inhalation quality measure. For example, at least one of the determined inhalation index and/or the X-ray image inhalation quality measure may be output on a display.

Figure 5:
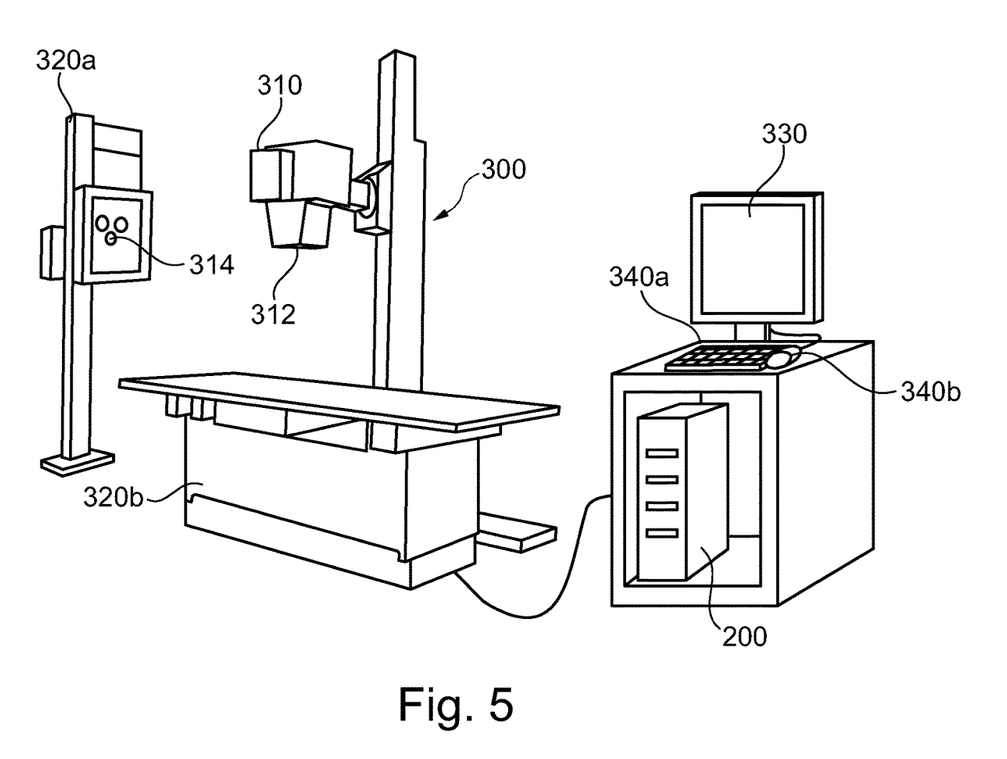
FIG. 5 depicts an exemplary implementation of an X-ray imaging system according to some embodiments of the present disclosure.

FIG. 5 illustrates an exemplary implementation of an X-ray imaging system 300 according to some embodiments of the present disclosure.

The X-ray imaging system 300 comprises an X-ray image acquisition device 310 with an X-ray source 312 and an X-ray detector 314. The X-ray source 312, e.g., rotating anode generators, may be positioned so that radiation is emitted in the direction of an X-ray detector 314, e.g., pixelated flat-panel X-ray detectors, where it is received. Optionally, the X-ray detector 314 may be located in a free-standing detector 320a, or a bed 320b. Thus, the thorax of a patient may be imaged in the standing, or sitting position.

The X-ray detector 310 may be connected to the apparatus 200 via a physical cable or wirelessly. In the exemplary example in FIG. 5, the apparatus 200 is a personal computer (PC). In another example, the apparatus 200 may be a server with a more powerful computing power to provide the service to multiple users to perform image quality assessment in many examination rooms. In other words, the image quality assessment algorithm may be made available on a server, e.g., a cloud server. In this case, the chest X-ray image taken by the X-ray imaging device 310 may be sent to the apparatus 200 configured to be a remote server, and the inhalation index, and optionally the X-ray image inhalation quality measure, are identified by the remote server. The corresponding results may be sent to a PC or a mobile device for being displayed to the user. In a further example, the image quality assessment algorithm may be made available to a mobile apparatus, e.g., a mobile computing device.

Optionally, the apparatus 200 may be configured to output at least one of the determined inhalation index and the X-ray image inhalation quality measure to a user via an output 330. In the exemplary example, the output 330 is a display. In other examples, the output may be a lamp, or a simple audible warning.

Optionally, the apparatus 200 may be provided with a user interface 340, such as a keyboard 340a and a mouse 340b. Further examples of the user interface may include, but not limited to, a touch screen and a joy stick arrangement. The user interface 340 may allow the user to define the score assigning rule and/or the X-ray image inhalation quality monitoring rule. The user interface 340 may be arranged remotely away from the X-ray imaging device 310, for instance outside the imaging room. Alternatively, the user interface may be arranged inside the room.

In use, a region of interest of a patient is positioned in front of the X-ray source 312. The X-ray source 312 is activated, e.g., via the user interface 340, and an exposure of the patient is made. The apparatus 200 assesses the quality of the image as described above. The apparatus 200 yields an inhalation index, and optionally an X-ray image inhalation quality measure, which is then output to a user on the display 330. In this way, a more reliable and easier assessable determination of the image quality of a chest X-ray image is achieved. The computation of the inhalation index for each chest X-ray image may be carried out without human supervision or interference, thereby avoiding the dependency upon variations or biases in the skill level of different system operators.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A computer implemented method for X-ray image inhalation quality monitoring, comprising:
   receiving a chest X-ray image of a patient;
   detecting rib bones in the chest X-ray image;
   identifying a plurality of intercostal spaces each representing a space between adjacent detected rib bones;
   detecting a diaphragm in the chest X-ray image and generating a diaphragm line comprising a plurality of points representing a path of a diaphragm in the chest X-ray image;
   assigning a point score to each point of the diaphragm line using a score assigning rule, wherein the score assigning rule defines a correspondence in the image between a point of the diaphragm line and an intercoastal space; and
   determining an inhalation index based on the point scores of the points of the diaphragm line.

2. The method according to claim 1, further comprising:
   comparing the determined inhalation index with a predetermined X-ray image inhalation quality monitoring rule specifying an image inhalation state in terms of the inhalation index, and providing an X-ray image inhalation quality measure based on the comparison.

3. The method according to claim 1, further comprising building a statistical atlas by co-registration of training images that comprise a plurality of chest X-ray images of one or more patients; and
   registering the statistical atlas with the chest X-ray image of the patient to build a patient specific rib-bone model of the patient.

4. The method according to claim 3, wherein the plurality of intercostal spaces is identified in the patient specific rib-bone model.

5. The method according to claim 3, further comprising mapping the detected diaphragm into the patient specific rib-bone model to generate the diaphragm line based on the registration.

6. The method according to claim 1, wherein the inhalation index is determined based on the point scores of the points of a right lung diaphragm line representing a path of the diaphragm in a right lung field portion and/or a left lung diaphragm line representing a path of the diaphragm in a left lung field portion.

7. The method according to claim 1, further comprising:
   labelling the plurality of intercostal spaces with intercostal labels; and/or
   labelling the detected rib bones with rib labels; wherein the score assigning rule defines:
   a correspondence between point scores and intercostal labels; and/or
   a correspondence between point scores and rib labels.

8. The method according to claim 1, wherein the score assigning rule further defines a correspondence between point scores and a spatial relation of a point in an intercostal space with respect to two detected rib bones that define the intercostal space; or wherein the score assigning rule provides interpolated rib labels and/or interpolated intercostal labels at each position in the statistical atlas such that a point score can be obtained for a given image pixel of the chest X-ray image by registering the statistical atlas with the chest X-ray image.

9. The method according to claim 1, wherein the inhalation index comprises at least one of measures of central tendency of the point scores of the diaphragm line.

10. An apparatus for X-ray image inhalation quality monitoring, comprising:
- an input configured to receive a chest X-ray image of a patient; and
- a processor configured to:
    - detect rib bones in the chest X-ray image;
    - identify a plurality of intercostal spaces each representing a space between adjacent detected rib bones;
    - detect diaphragm in the chest X-ray image and generate a diaphragm line comprising a plurality of points representing a path of a diaphragm in the chest X-ray image;
    - assign a point score to each point of the diaphragm line using a score assigning rule, wherein the score assigning rule defines a correspondence in the image between a point of the diaphragm line and an intercoastal space; and
    - determine an inhalation index based on the point scores of the points of the diaphragm line.

11. The apparatus according to claim 10, wherein the processor is further configured to compare the determined inhalation index with a pre-determined X-ray image inhalation quality monitoring rule specifying an image inhalation state in terms of the inhalation index, and provide an X-ray image inhalation quality measure based on the comparison.

12. The apparatus according to claim 10, further comprising:
- an output configured to output the determined inhalation index and/or an X-ray image inhalation quality measure.

13. A non-transitory computer-readable medium having executable instructions stored thereon which, when executed by at least one processor, cause the at least one processor to perform a method for X-ray image inhalation quality monitoring, the method comprising:
- receiving a chest X-ray image of a patient;
- detecting rib bones in the chest X-ray image;
- identifying a plurality of intercostal spaces each representing a space between adjacent detected rib bones;
- detecting a diaphragm in the chest X-ray image and generating a diaphragm line comprising a plurality of points representing a path of a diaphragm in the chest X-ray image;
- assigning a point score to each point of the diaphragm line using a score assigning rule, wherein the score assigning rule defines a correspondence in the image between a point of the diaphragm line and an intercoastal space; and
- determining an inhalation index based on the point scores of the points of the diaphragm line.

* * * * *